US 6,598,084 B1

(12) United States Patent
Edwards et al.

(10) Patent No.: US 6,598,084 B1
(45) Date of Patent: Jul. 22, 2003

(54) METHODS AND APPARATUS FOR PROCESSING, TRANSMITTING, AND RECEIVING DATA FROM A MODULAR ELECTRONIC MEDICAL DEVICE

(75) Inventors: Eric D. Edwards, Ringwood, NJ (US); Masayuki Kano, Washington Township, NJ (US)

(73) Assignees: Sony Corporation, Park Ridge, NJ (US); Sony Electronics, Inc., Park Ridge, NJ (US)

( * ) Notice: Subject to any disclaimer, the term of this patent is extended or adjusted under 35 U.S.C. 154(b) by 0 days.

(21) Appl. No.: 09/250,274

(22) Filed: Feb. 16, 1999

(51) Int. Cl.[7] ............................................. G06F 13/00
(52) U.S. Cl. ....................... 709/230; 709/205; 709/240; 433/29; 713/400; 713/600; 710/129; 710/131
(58) Field of Search ................................ 709/205, 230, 709/240; 433/29; 713/400, 600; 710/129, 131; G06F 17/60, 13/00

(56) References Cited

U.S. PATENT DOCUMENTS

| 4,112,950 A | | 9/1978 | Pike |
| 4,576,183 A | | 3/1986 | Plicchi et al. |
| 4,764,870 A | | 8/1988 | Haskin |
| 4,809,697 A | * | 3/1989 | Causey et al. |
| 4,944,302 A | | 7/1990 | Hernandez et al. |
| 5,005,126 A | | 4/1991 | Haskin |
| 5,020,135 A | * | 5/1991 | Kasparian et al. |
| 5,442,389 A | * | 8/1995 | Blahut et al. |
| 5,482,050 A | | 1/1996 | Smokoff et al. |
| 5,488,537 A | | 1/1996 | Heald et al. |
| 5,529,063 A | | 6/1996 | Hill |
| 5,586,556 A | * | 12/1996 | Spivey et al. |
| 5,619,991 A | | 4/1997 | Sloane |
| 5,642,157 A | | 6/1997 | Shibanuma |
| 5,730,146 A | | 3/1998 | Itil et al. |
| 5,832,450 A | | 11/1998 | Myers et al. |
| 5,987,519 A | * | 11/1999 | Peifer et al. ................ 709/230 |
| 6,032,261 A | * | 2/2000 | Hulyalkar .................... 713/400 |
| 6,065,119 A | * | 5/2000 | Sandford et al. ........... 713/200 |
| 6,093,019 A | * | 7/2000 | Morandi et al. .............. 433/29 |
| 6,112,224 A | | 8/2000 | Peifer et al. ................ 709/202 |

FOREIGN PATENT DOCUMENTS

| AU | 200030009 A | * | 9/2000 | ........... G06F/17/60 |
| WO | WO 200049549 A1 | * | 8/2000 | ........... G06F/17/60 |

OTHER PUBLICATIONS

Dialog Abstract: Fromm, I., Local Area Networks—high speed networks for office communication, Bulletin de l'Association Suisse des Electriciens, vol. 74, No. 11, pp. 585–589, Jun. 4, 1983.

* cited by examiner

Primary Examiner—Cuong H. Nguyen
(74) Attorney, Agent, or Firm—Finnegan, Henderson, Farabow, Garrett & Dunner, L.L.P.

(57) ABSTRACT

This disclosure describes systems and methods for processing medical information from an electronic medical device connected to a patient via a serial bus at one site for transmission and receipt over a network to a remote diagnostic site or medical processing center for a medical diagnosis. The systems and methods encompass any electronic medical device that produces a signal that may be communicated via a serial bus. The systems and methods prepare the signal from the serial bus for transmission over a network and entail the receipt of the signal at a remote diagnostic site or medical processing center. At the remote diagnostic site or medical processing center, the signal is then presented to a physician or other medical technician for analysis and diagnosis. After diagnosis of the signal at the remote diagnostic site or medical processing center the diagnosis may be provided to the patient. Systems and methods consistent with the present invention are compatible with electronic medical devices that communicate a signal via a serial bus, including but not limited to a universal serial bus, a high performance serial bus according to the IEEE 1394-1995 standard, or a high performance serial bus according to the IEEE P1394.1 standard.

48 Claims, 11 Drawing Sheets

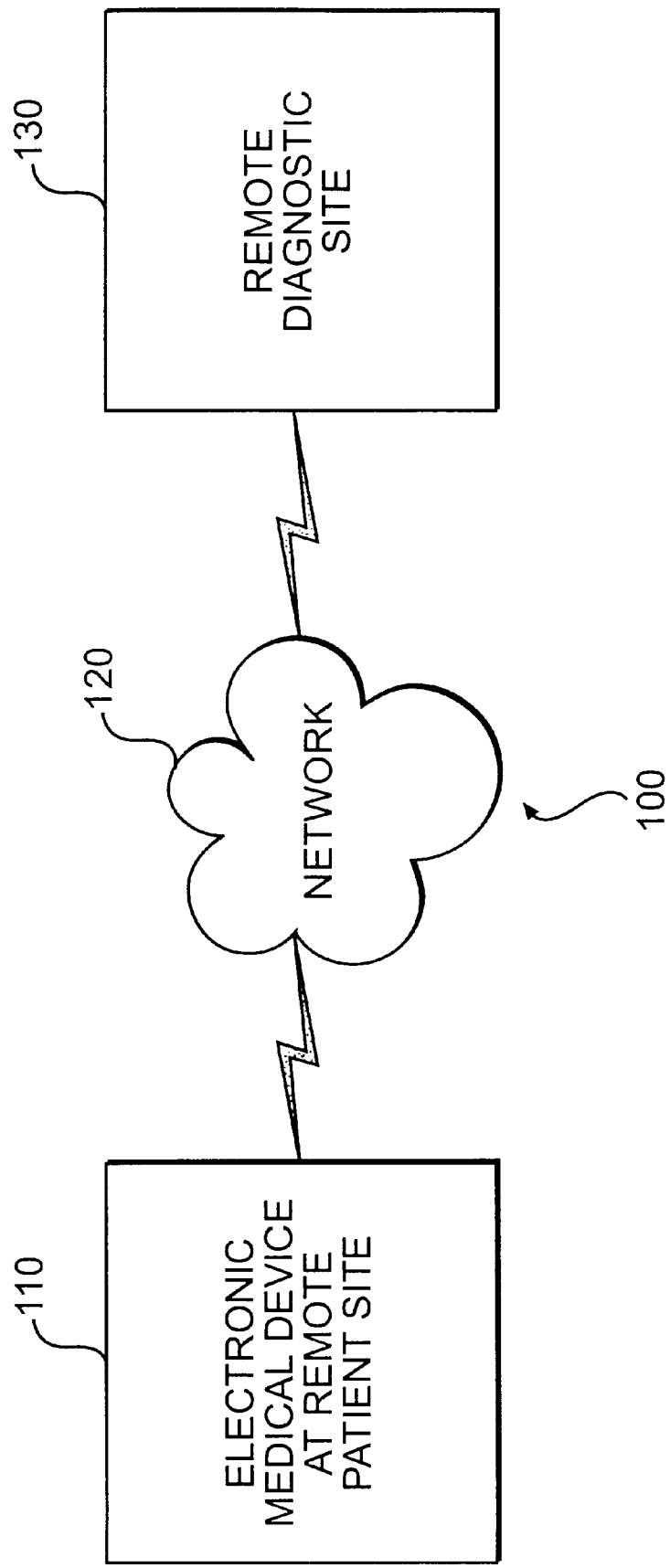

METHODS AND APPARATUS FOR PROCESSING, TRANSMITTING, AND RECEIVING DATA FROM A MODULAR ELECTRONIC MEDICAL DEVICE

I. BACKGROUND OF THE INVENTION

A. Field of the Invention

The present invention relates to a method and apparatus for processing medical information from an electronic medical device for transmission and receipt over a network. More particularly, the invention relates to methods and apparatus for processing medical information via a serial bus from an electronic medical device at a remote patient site for transmission and receipt over a network to a remote diagnostic site or a medical processing center.

B. Description of the Related Art

The advance of medical technology has now made feasible the analysis and potential diagnosis of certain medical conditions from a patient's home. Many of the electronic medical devices that were once only available at a doctor's office or hospital are now commonly available for purchase and use at home. These devices not only include simple electronic medical devices, such as electronic blood pressure devices electronic thermometers, and electronic stethoscopes, but such devices also include more advanced electronic medical devices, such as EKGs and EEGs.

Further, many electronic optical devices are also now affordable and available for easy use and connectivity for medical purposes. These electronic optical devices can also provide the level of detail necessary for a physician or medical technician to analyze and diagnose medical conditions from images produced by the devices. These devices include digital cameras and digital camcorders.

In addition, with the advent and development of digital network technology, the integration of medicine with digital networks provides new opportunities for medical analysis and diagnosis. Indeed, by the use of a network, such as the Internet, the capability now exists for a patient to seek an instant, on-line consultation with a physician. For example, some of the present systems allow a patient to transmit medical information from the patient's home over the Internet, have the medical information received for analysis at another location, and obtain a diagnosis of a medical condition from an analysis of the medical information by a physician or medical technician.

However, these conventional systems and methods primarily include receiving a textual medical description from a patient over a network and then providing for an analysis and diagnosis based on that textual medical description. Therefore, these conventional systems and methods do not provide for the processing of the signals obtained from an electronic medical device and the integration of these signals with the same system or method utilizing a network for communications.

Further, while some of the conventional systems and methods do include the transmission of certain medical data over a network, in most cases, the medical data does not represent the source signal of an electronic medical device. Instead, the data only represents the textual results of a medical test, even though the medical test may have been performed by an electric medical device.

Finally, even if the conventional systems and methods provide for the transmission and receipt of signals from electronic medical devices, none of the conventional systems and methods provide for the integration of an electronic medical device with an interface at a patient's home via a serial bus. In particular, developments in serial bus technology has only recently made the processing of signals from an electronic medical device feasible for use over a digital network. Also, there is an absence of systems and methods for integrating this technology for medical purposes.

The conventional systems and methods are therefore disadvantageous and inefficient, because they do not provide for the processing of medical information from an electronic medical device via a serial bus at a remote patient site for transmission and receipt over a network to another location for analysis and diagnosis. Due to the absence of a system or method of processing, transmitting, and receiving medical information from an electronic medical device via a serial bus at a remote patient site over a network, there is a general need for such a system and method. There is also a need for a system and method that processes, transmits, and receives medical information via a serial bus at a remote patient site over a network to a remote diagnostic site or a medical processing center, where the information will be subject to analysis and diagnosis.

II. SUMMARY OF THE INVENTION

Methods and apparatus consistent with the present invention overcome the shortcomings of the conventional systems by processing medical information from an electronic medical device via a serial bus at a remote patient site for transmission and receipt over a network to a remote diagnostic site or a medical processing center.

In accordance with the purposes of the invention, as embodied and broadly described herein, one aspect of the invention includes a method of processing medical information obtained from an electronic medical device. This method comprises the stages of receiving medical information from the electronic medical device via a serial bus at a remote patient site, processing the medical information for transmission over a network, transmitting the medical information over the network, receiving the medical information at a remote diagnostic site over the network, processing the medical information for analysis and diagnosis at the remote diagnostic site, and making the medical information available at the remote diagnostic site for analysis and diagnosis.

In another aspect, the invention includes a method for processing medical information obtained from an electronic medical device, comprising the stages of inputting a digital signal representing medical information from the electronic medical device connected to a patient via a serial bus at a remote patient site, constructing a data packet containing the digital signal at the remote patient site for transmission over a network, transmitting the data packet at the remote patient site over the network. receiving the data packet at a medical processing center over the network, deconstructing the data packet at the medical processing center to obtain the digital signal, and transmitting the digital signal from the medical processing center to a diagnosis location for analysis and diagnosis by a physician or a medical technician.

In yet another aspect, the invention includes a method for preparing medical information obtained from an electronic medical device for transmission over a network, comprising the stages of inputting a signal representing medical information from the electronic medical device connected to a patient via a serial bus at a remote patient site, processing the medical information for transmission over a network, and transmitting the medical information at the remote patient site over the network.

In still another aspect, the invention includes a method for processing medical information obtained from an electronic medical device when received over a network, comprising the stages of receiving a data packet containing medical information over a network at a remote location, processing the data packet, and obtaining from the medical information a signal, which originated from an electronic medical device connected to a patient via a serial bus at a remote patient site.

Additional aspects of the invention are disclosed and defined by the appended claims. It is to be understood that both the foregoing general description and the following detailed description are exemplary and explanatory and are intended to provide further explanation of the invention as claimed.

III. BRIEF DESCRIPTION OF THE DRAWINGS

The accompanying drawings are included to provide a further understanding of the invention, are incorporated in and constitute a part of this specification, illustrate preferred embodiments of the invention, and, together with the description, serve to explain the principles of the invention.

In the drawings,

FIGS. 1A and 1B are block diagrams of two embodiments of an electronic medical device diagnostic system consistent with the principles of the present invention;

Figure 5A:
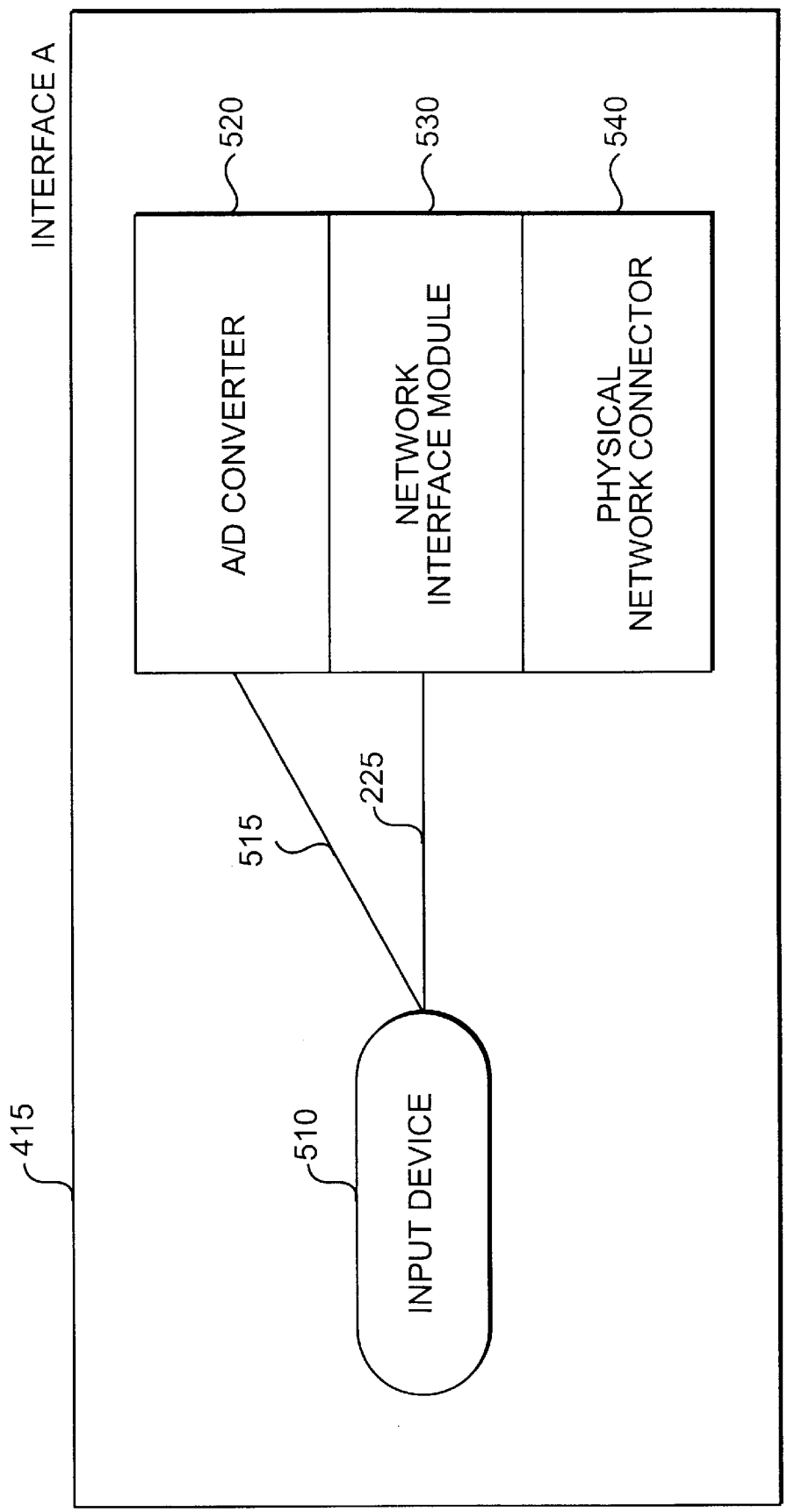
Figure 5B:
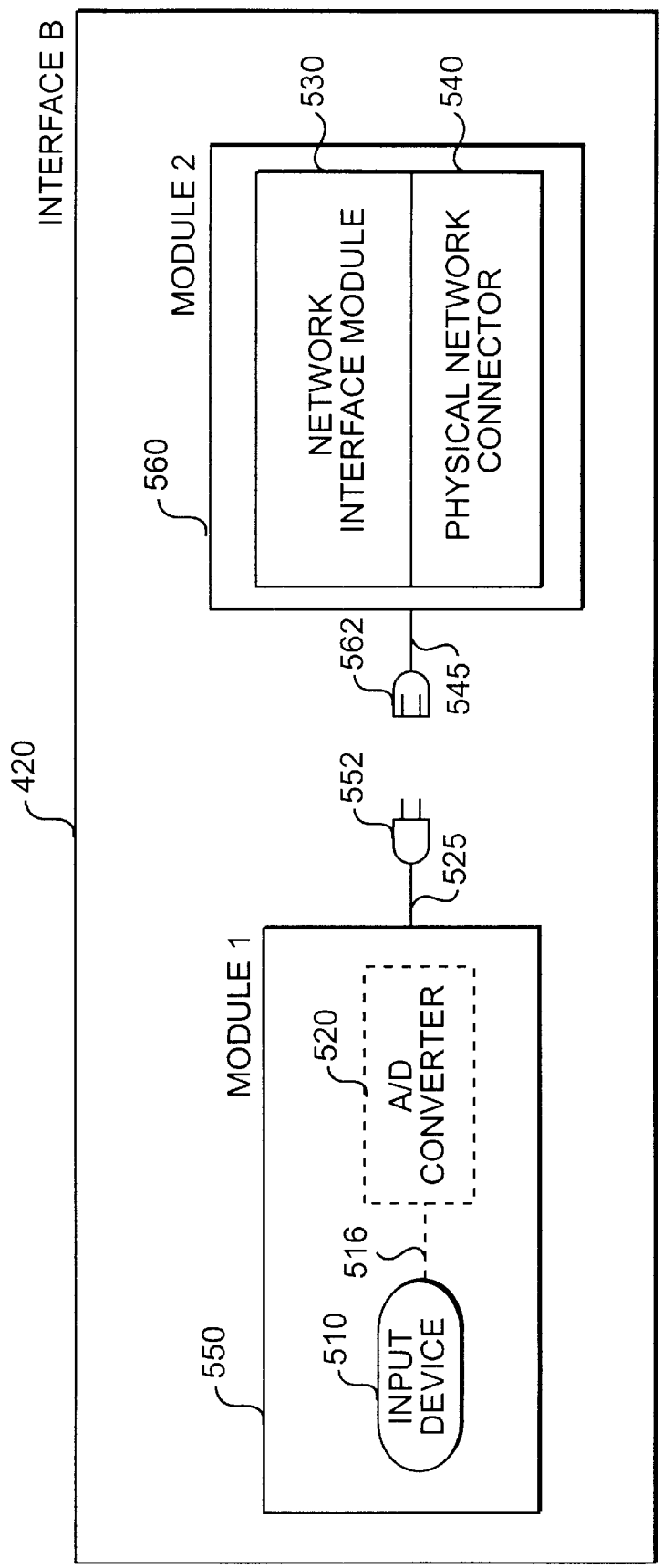
Figure 5C:
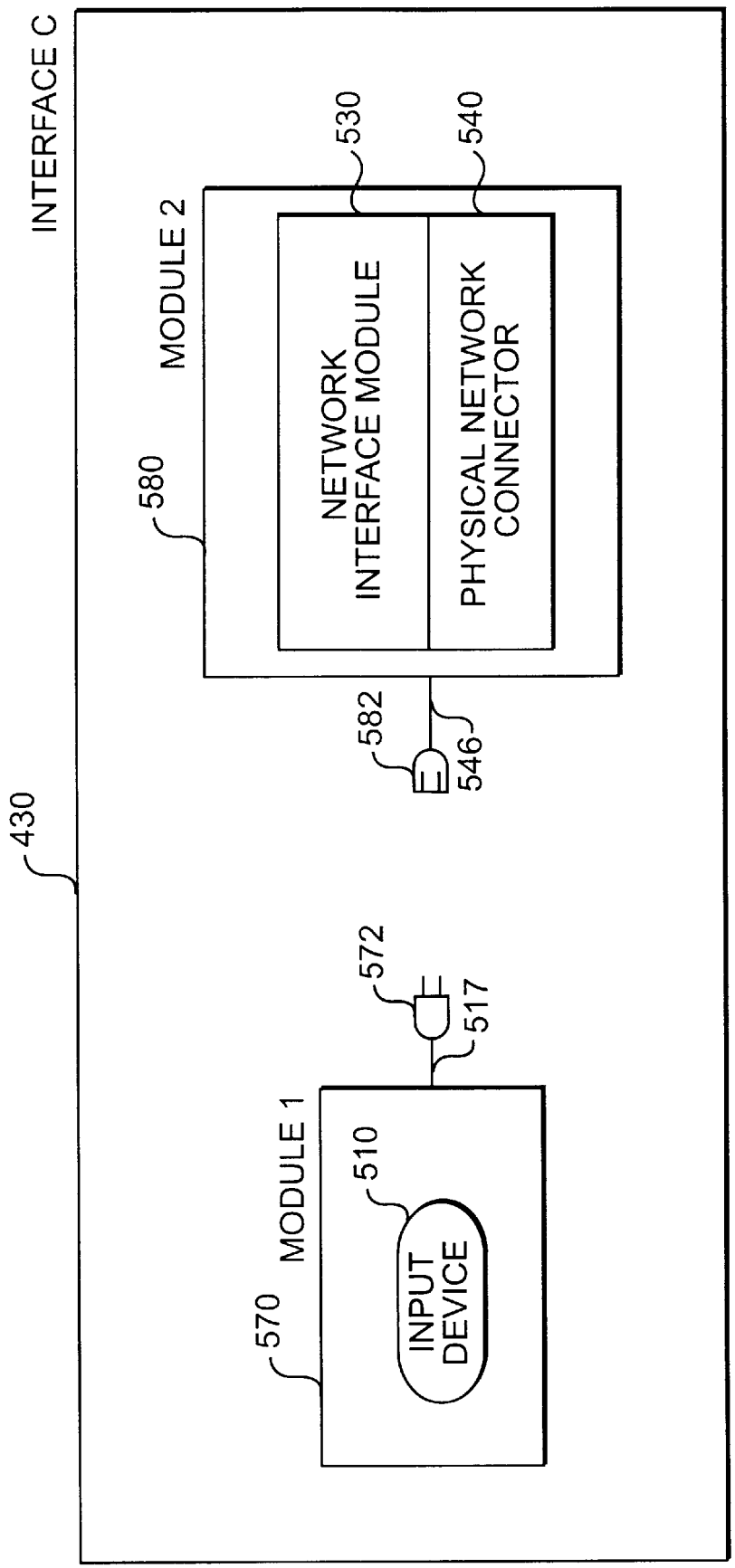
Figure 6:
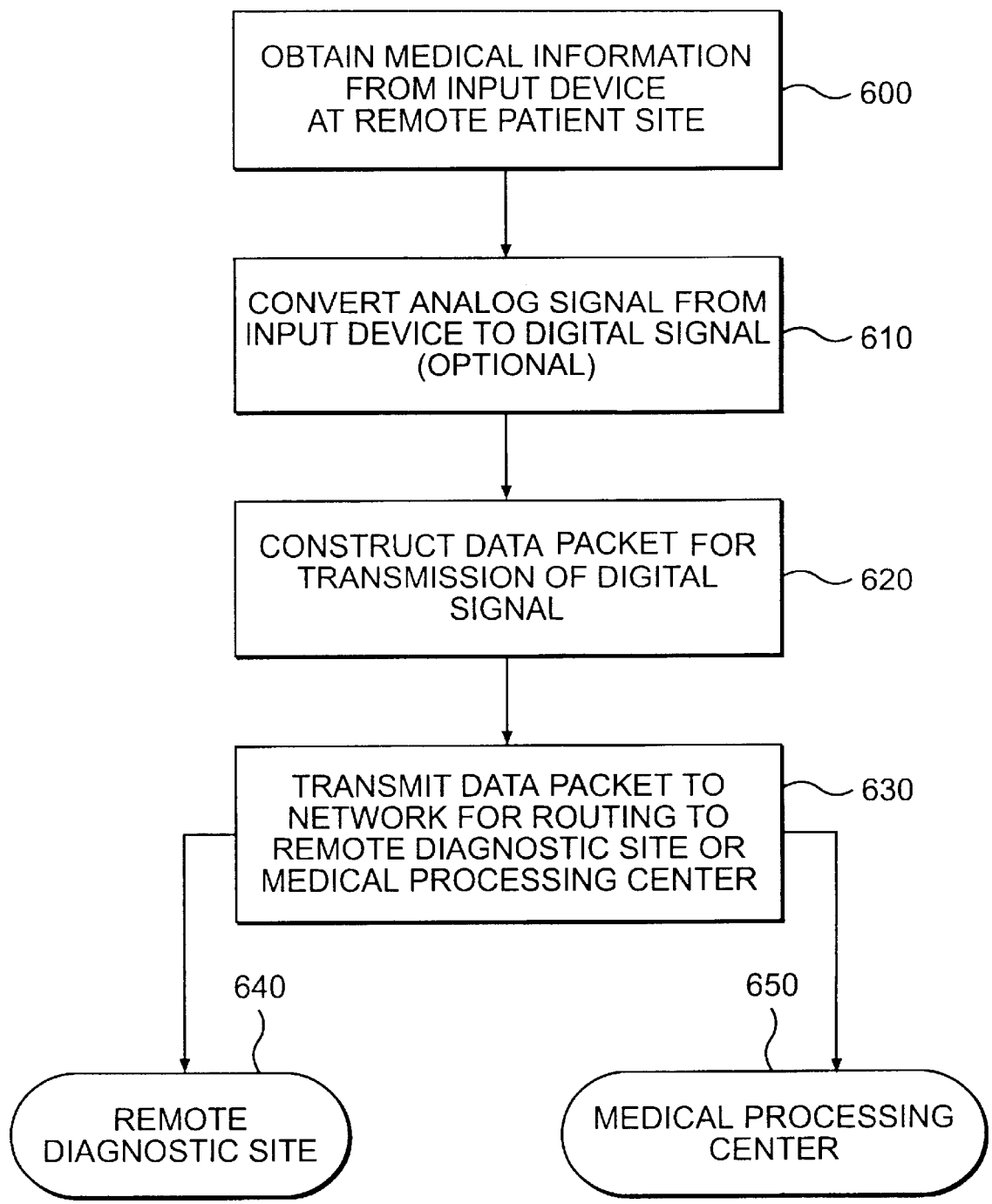
Figure 7:
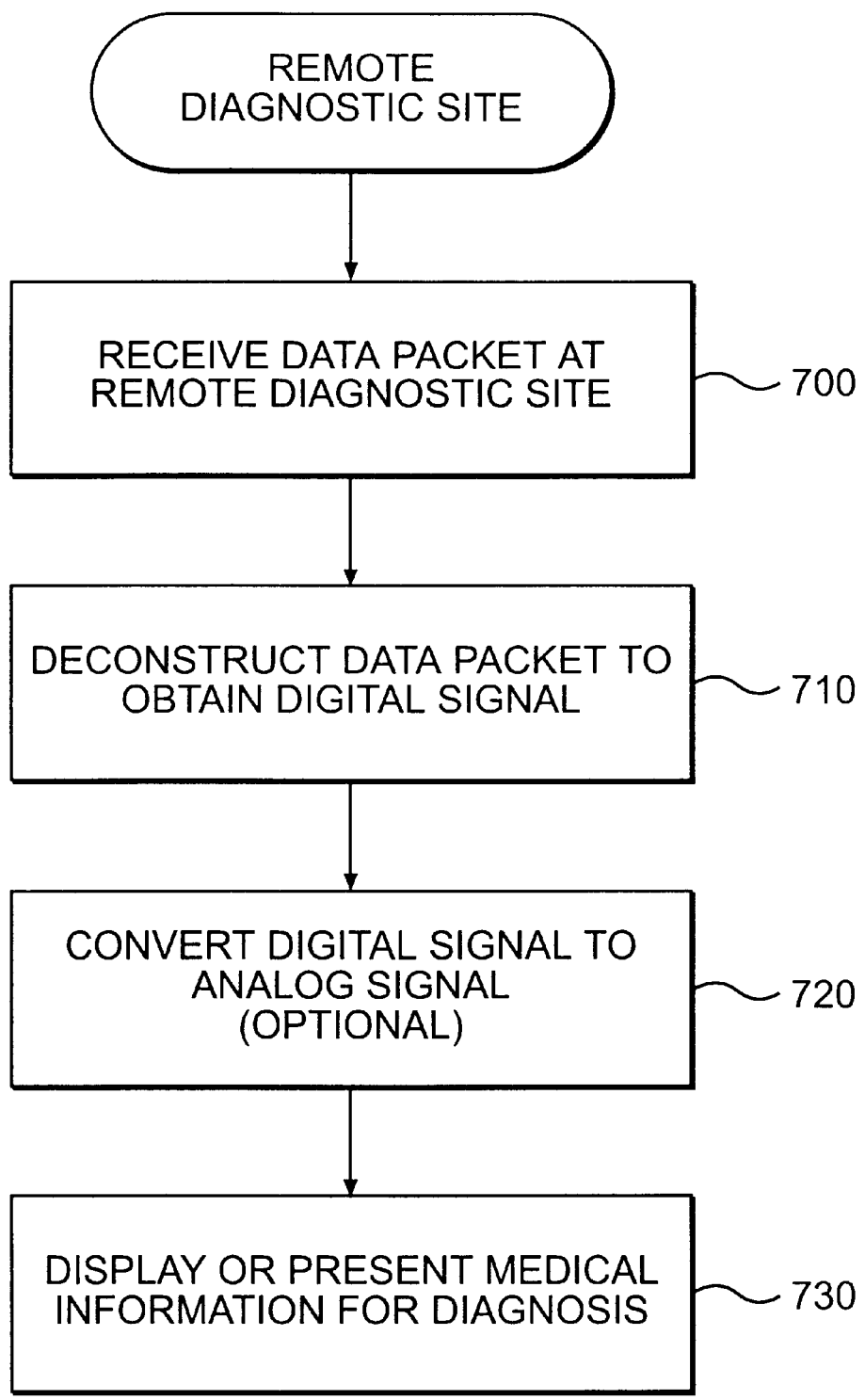
Figure 8:
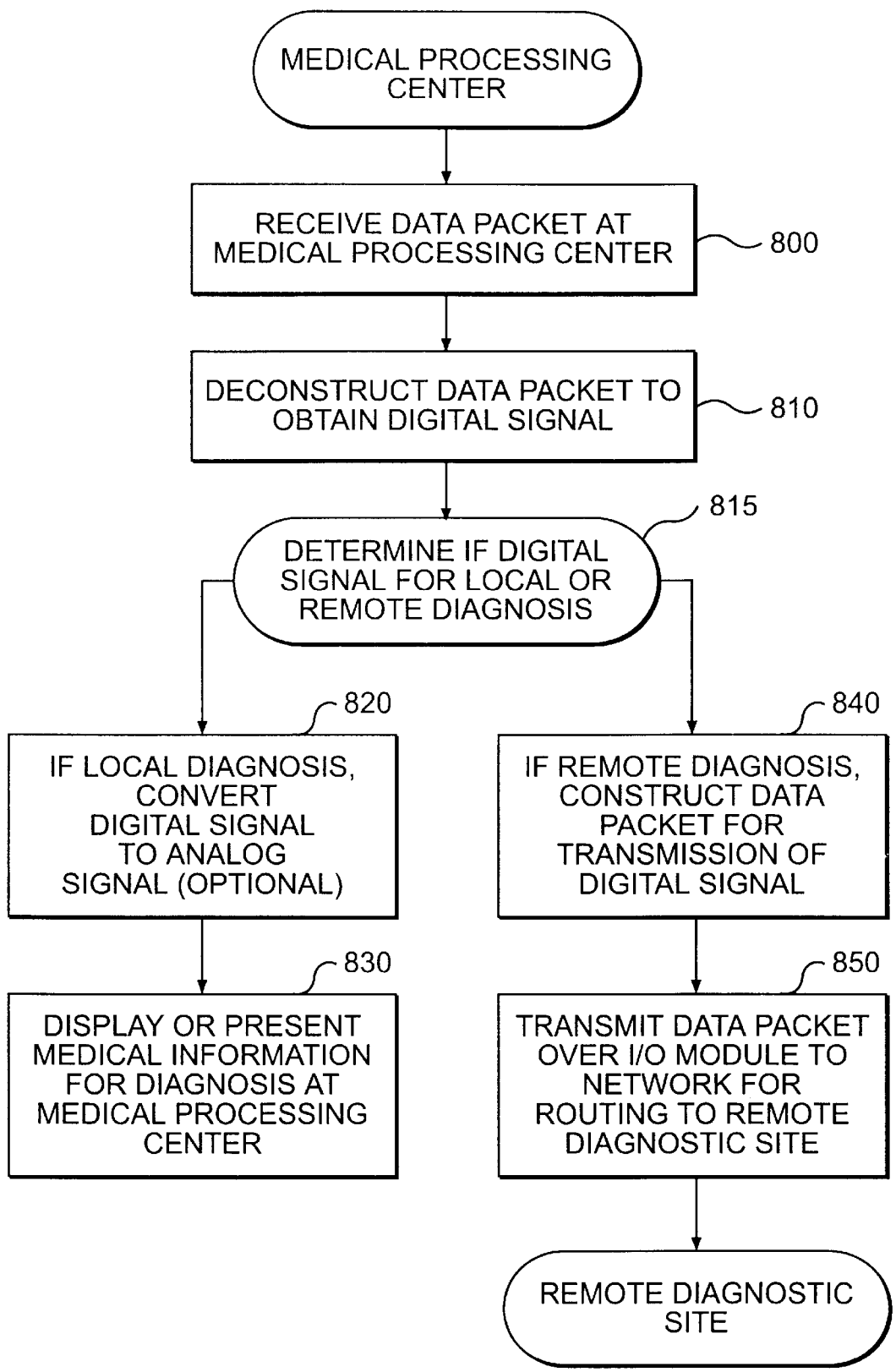

FIGS. 5A, 5B, and 5C are block diagrams of three alternative interfaces that may be present at a remote patient site in an electronic medical device diagnostic system in accordance with different embodiments of the present invention;

FIG. 6 is a flow diagram of a method for obtaining medical information from an input device at a remote patient site in accordance with one embodiment of the present invention;

FIG. 7 is a flow diagram of a method for receiving medical information at a remote diagnostic site in accordance with one embodiment of the present invention;

FIG. 8 is a flow diagram of a method for receiving medical information at a medical processing center in accordance with one embodiment of the present invention.

IV. DETAILED DESCRIPTION

A. Introduction

A system consistent with the principles of the present invention as disclosed herein provides for processing medical information obtained from an electronic medical device via a serial bus for transmission and receipt over a network. The system avoids the shortcomings of the present systems and methodologies by providing for the input of a signal from an electronic medical device via a serial bus at a remote patient site for transmission and receipt over a network in order to obtain an analysis and diagnosis of the medical information from another location. With the disclosed system, and as otherwise described herein, the transmission and receipt of medical information over a network for analysis and diagnosis may be made to either a remote diagnostic site or a medical processing center.

B. System

FIG. 1A illustrates a block diagram of an electronic medical device diagnostic system according to one embodiment of the present invention. System 100 comprises electronic medical device at remote patient site 110, network 120, such as, for example the Internet, and remote diagnostic site 130. Electronic medical device at remote patient site 110 may either transmit or receive over network 120, and similarly, remote diagnostic site 130 may also either transmit or receive over network 120. Electronic medical device at remote patient site 10 obtains medical information from an electronic medical device for transmission over network 120 and receipt by remote diagnostic site 130. Remote diagnostic site 130 may then analyze and diagnose the medical information and, optionally, transmit a diagnosis via network 120 to electronic medical device at remote patient site 110. Due to the potential of immediate responses made possible by system 100, the transmission of medical information from the electronic medical device at remote patient site 110 to remote site 130 via network 120 provides for virtually instantaneous analysis and diagnoses of any medical condition that may be accessed or monitored by an electronic medical device.

Figure 1B:
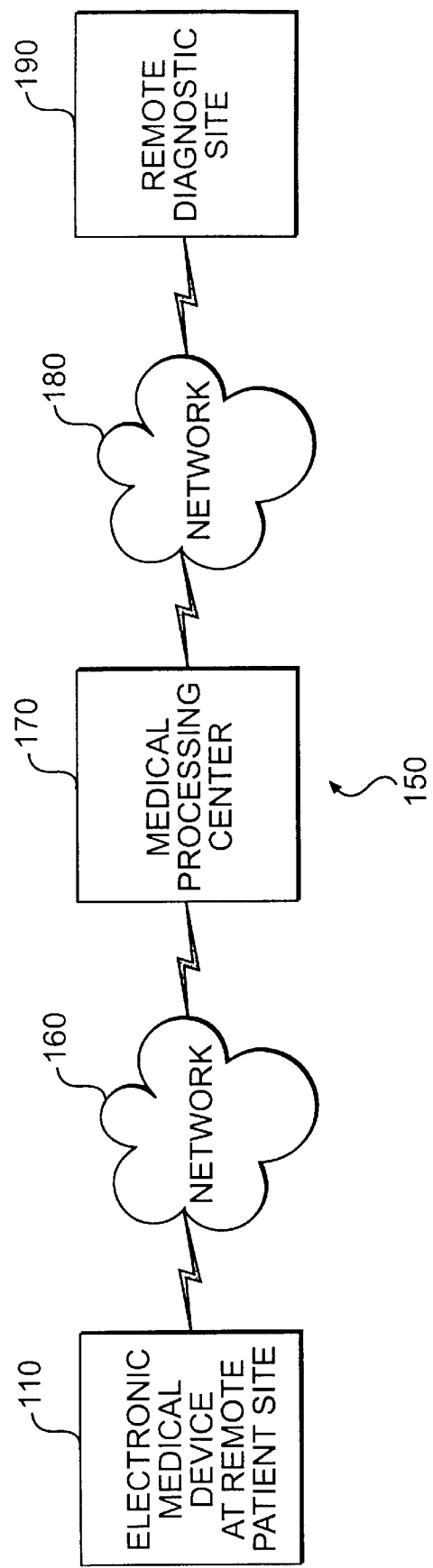

FIG. 1B illustrates a block diagram of an electronic medical device diagnostic system in accordance with another embodiment of the present invention. In this embodiment, system 150 comprises electronic medical device at remote patient site 110, network 160, medical processing center 170, network 180, and remote diagnostic site 190. System 150 is similar to system 100, except that medical information obtained from the electronic medical device at remote patient site 110 is transmitted to remote diagnostic site 190 through medical processing center 170. Also, the transmission and receipt of medical information originating from the electronic medical device at remote patient site 110 occurs via both network 160 and network 180. However, although FIG. 1B depicts network 160 and network 180 as separate networks, network 160 and network 180 may also comprise the same network. System 150 may be advantageous to system 100 because medical processing center 170 may act as a router for medical information. In this capacity, medical processing center 170 may determine where to send the medical information among a multiplicity of remote diagnostic sites 190. Of course, medical processing center 170 may also have the capability to analyze and diagnose medical information locally. If so, medical processing center 170 and remote diagnostic site 190 coexist at the same location.

Figure 2:
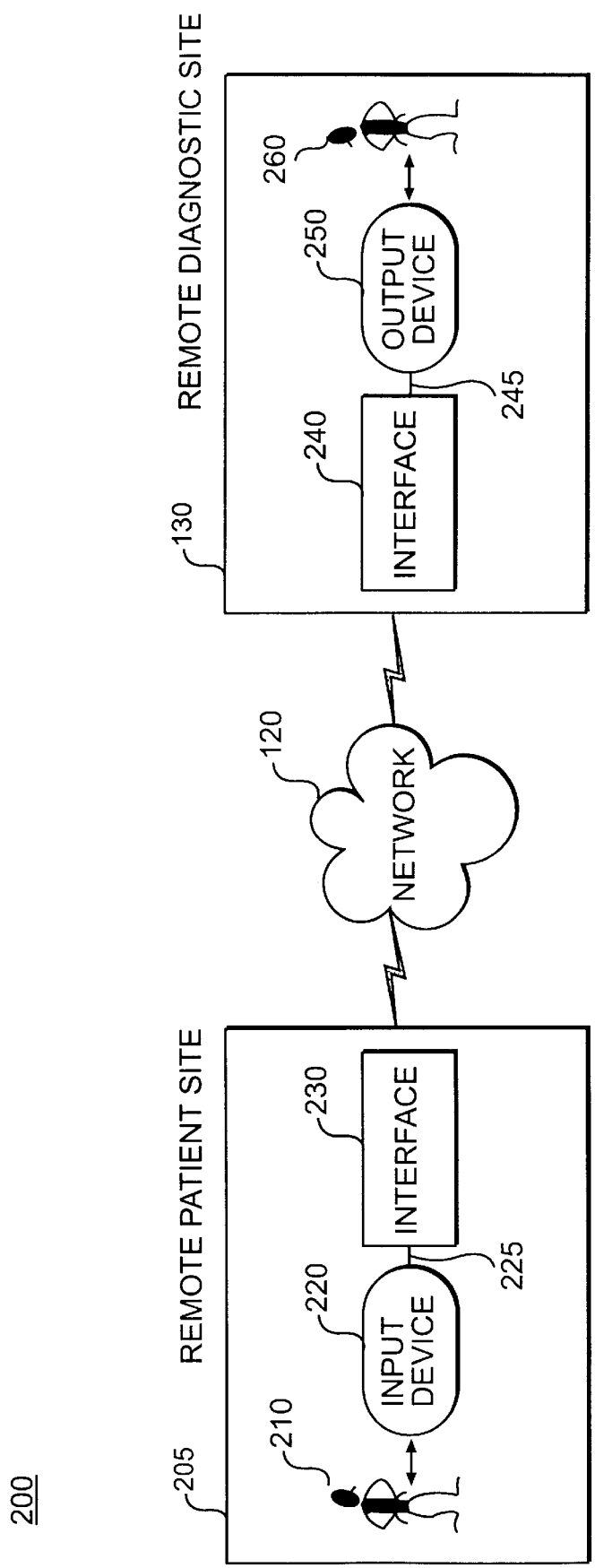
FIG. 2 is a block diagram of an electronic medical device diagnostic system in accordance with another embodiment of the present invention.

FIG. 2 illustrates a block diagram of an electronic medical device diagnostic system in accordance with still another embodiment of the present invention. FIG. 2 depicts an embodiment of an electronic medical device diagnostic system, which is similar to the system shown in FIG. 1A. In this embodiment, system 200 comprises remote patient site 205, such as, for example, a patient's home, network 120, and remote diagnostic site 130. However, FIG. 2 also delineates the components of remote patient site 205 and remote diagnostic site 130. For example, remote patient site 205 comprises patient 210, input device 220, serial bus 225, and interface 230. And, remote diagnostic site 130 comprises interface 240, bus 245, output device 250, and physician or medical technician 260. Remote patient site 205 and remote diagnostic site 130 comprise essentially the same basic components. Remote patient site 205 contains patient 210, which interacts with input device 220, which connects to interface 230 via serial bus 225. Similarly, remote site 130 comprises physician 260, which interacts with output device 250, which connects to interface 240 via bus 245. As noted above, remote patient site 205 and remote diagnostic site 130 may both transmit and receive information. Thus, patient 210 may both input medical information into input device 220 via serial bus 225 to interface 230 or receive a diagnosis from interface 230 via serial bus 225 to an output device (not shown). Also, physician 260 may receive medical information from output device 250 via bus 245 to interface 240 and input a diagnosis in an input device (not shown) via bus 245 to interface 240 for transmission to patient 210 over network 120.

In this embodiment, system 200 includes a serial bus 225 and a bus 245. Notably, system 200 includes a serial bus for serial bus 225, but system 200 includes any type of bus for bus 245. In one embodiment, serial bus 225 is a universal serial bus (USB). In another embodiment, serial bus 225 is a high performance serial bus according to the IEEE 1394-1995 standard. In still another embodiment, serial bus 225 is a high performance serial bus according to the IEEE P1394.1 standard. According to the present invention, as shown in FIG. 2, a serial bus is used at the remote patient site, so that the electronic medical device diagnostic system receives a satisfactory signal at the remote patient site for processing and eventual transmission over network 120 to remote diagnostic site 130 for analysis and diagnosis. Of course, a serial bus of a type other than those described above may also be used for serial bus 225 in systems and methods consistent with the present invention.

Figure 3:
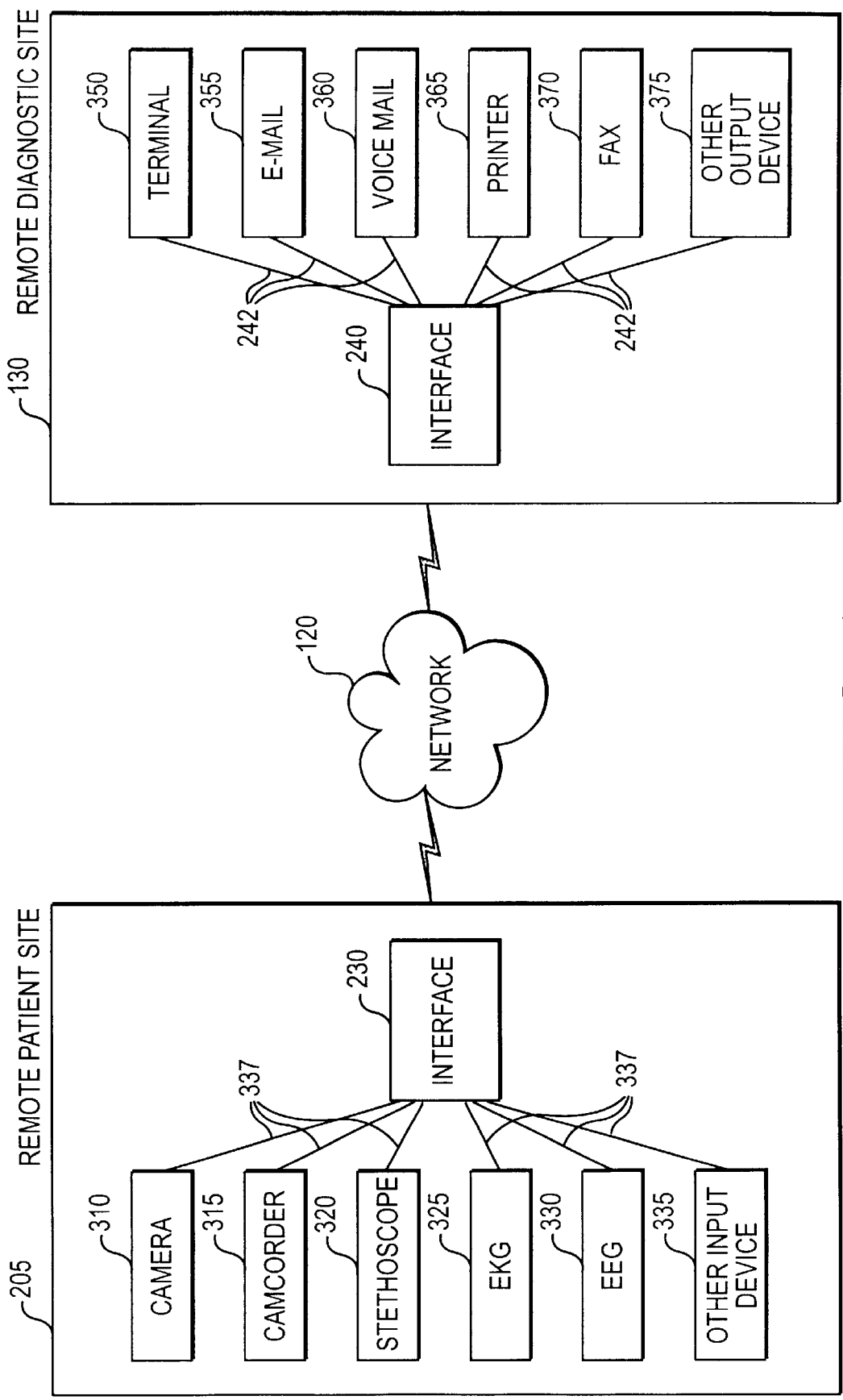
FIG. 3 is a block diagram depicting some of the interface options for an electronic medical device diagnostic system in accordance with one embodiment of the present invention.

FIG. 3 illustrates a block diagram of the interface options for an electronic medical device diagnostic system in accordance with one embodiment of the present invention. In particular, FIG. 3 depicts an embodiment of interface options for an electronic medical device diagnostic system, such as the system shown in FIG. 2. In this embodiment, system 300 comprises remote patient site 205, network 120, and remote diagnostic site 130. Remote patient site 205 comprises camera 310, camcorder 315, stethoscope 320, EKG 325, EEG 330, other input device 335, serial bus connections 337, and interface 230. Remote diagnostic site 130 comprises terminal 350, e-mail 355, voice mail 360, printer 365, fax 370, other output device 375, bus connections 242, and interface 240. As indicated by other input device 335, an unlimited number of input devices may be connected to interface 230 at remote patient site 205. Similarly, as indicated by other output device 375, an unlimited number of output devices may be connected to interface 240 at remote diagnostic site 130. As described above, because interface 230 and interface 240 may both transmit and receive over network 120, via serial bus connections 337 and bus connections 242, respectively, input devices 310–335 may also exist at remote diagnostic site 130 connected to interface 240, and output devices 350–375 may also exist at remote patient site 205 connected to interface 230.

Figure 4:
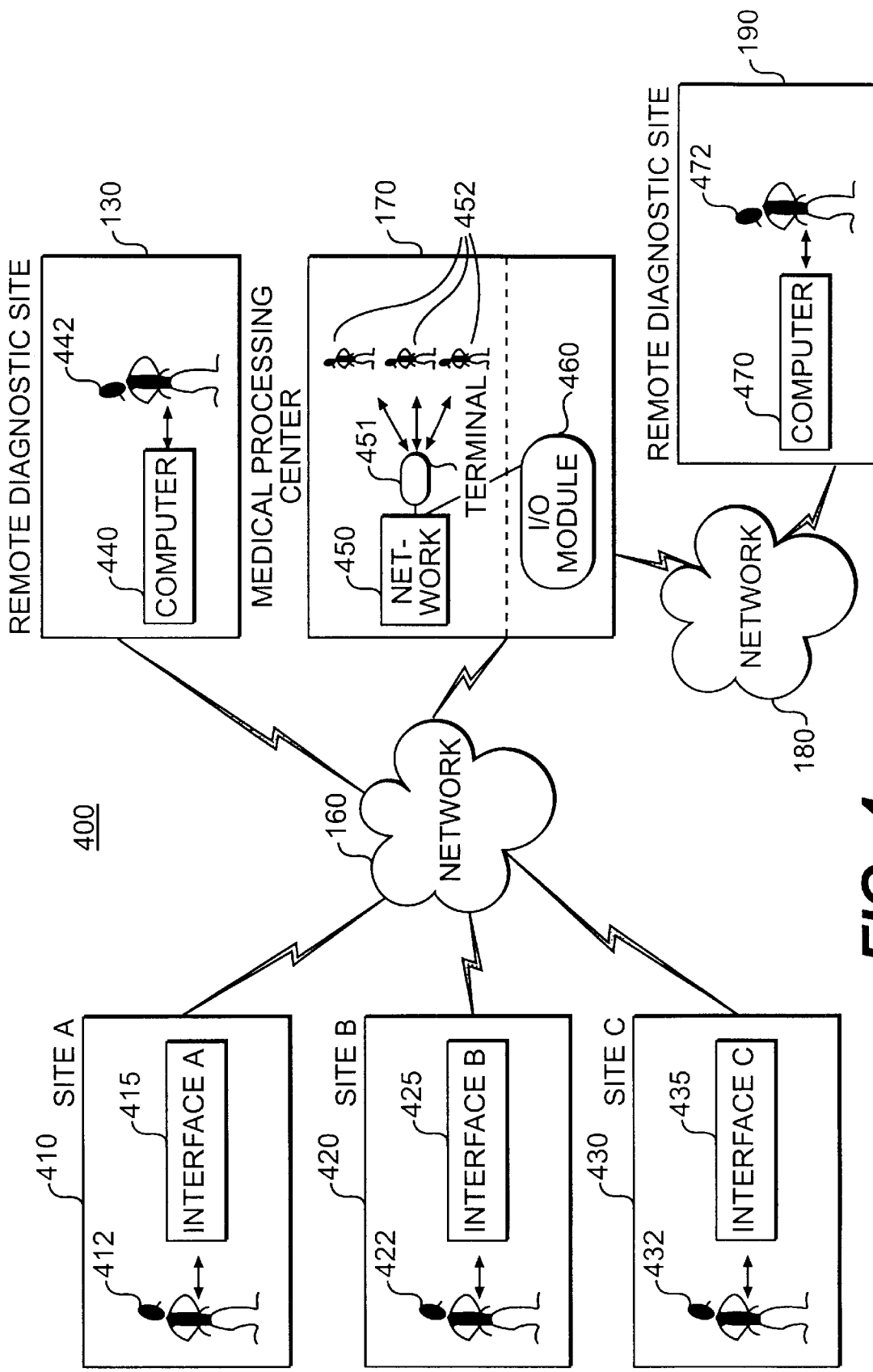
FIG. 4 is a block diagram of an electronic medical device diagnostic system in accordance with another embodiment of the present invention.

FIG. 4 illustrates a block diagram of an electronic medical device diagnostic system in accordance with an alternative embodiment of the present invention. FIG. 4 depicts an electronic medical device diagnostic system that incorporates the systems depicted by both FIGS. 1A and 1B. In this embodiment, system 400 comprises site A 410, site B 420, site C 430, network 160, remote diagnostic site 130, medical processing center 170, network 180, and remote diagnostic site 190. System 400 depicts site A 410, site B 420, and site C 430 to demonstrate some of the interface configurations according to the present invention. Site A 410 comprises patient 412 and interface A 415. Site B 420 comprises patient 422 and interface B 425. Site C 430 comprises patient 432 and interface C 435. Some of the alternative configurations available for interface A 415, interface B 425, and interface C 435 are described in FIGS. 5A–5C.

As shown in FIG. 4, for medical information originating from any of site A 410, site B 420, or site C 430, the transmission of such medical information to a remote location occurs via network 160. The medical information may then be received by either remote diagnostic site 130 or medical processing center 170.

If the medical information is received by remote diagnostic site 130, the information may be displayed at remote diagnostic site 130 via an interface, such as, for example, computer 440. Physician or medical technician 442 may then interact with computer 440 to obtain the medical information for analysis and diagnosis.

If the medical information is received at medical processing center 170, the information may be displayed at an interface, such as, for example, terminal 451 connected to network 450. Physicians or medical technicians 452 may then review the medical information for analysis and diagnosis. Medical processing center 170 may optionally contain I/O module 460. I/O module 460 is also connected to network 450 and provides for the subsequent transmission of medical information to a remote diagnostic site, such as, for example, remote diagnostic site 190 via network 180. Remote diagnostic site 190 is similar to remote diagnostic site 130. Remote diagnostic site 190 receives the medical information via an interface, such as, for example, computer 470. Physician or medical technician 472 interacts with computer 470 to obtain the medical information for analysis and diagnosis. Notably, an unlimited number of remote diagnostic sites 130 and 190 or medical processing centers 170 may be connected to the electronic medical device diagnostic system via networks 160 and 180.

FIG. 5A illustrates a block diagram of an interface for preparing medical information for transmission over an electronic medical device diagnostic system according to one embodiment of the present invention. FIG. 5A depicts interface A 415 from FIG. 4. In this embodiment, interface A 415 comprises input device 510, connector 515, serial bus 225, analog/digital (A/D) converter 520, network interface module 530, and physical network connector 540. As shown in FIG. 5A, components 510 through 540 are contained within a single unit. Input device 510 receives a signal from the electronic medical device. If the signal is an analog signal, pursuant to the interface with input device 510 via connector 515, A/D converter 510 then converts the analog signal into a digital signal. If the signal is a digital signal, pursuant to the interface with input device 510 via serial bus 225, the digital signal is simply transmitted to network interface module 530. Network interface module 530 then prepares the digital signal for transmission over a network by creating a data packet. Physical network connector 540 provides the physical connection for interface A 415 to interface with a network. An example of interface A 415 is a single electronic medical device that interfaces with a computer. In this example, interface A 415 would prepare a signal received from an electronic medical device for transmission over a network, so that the computer would need not make additional changes to the signal before transmission over the network.

FIG. 5B illustrates a block diagram of an interface for preparing medical information for transmission over an electronic medical device diagnostic system according to an alternative embodiment of the present invention. FIG. 5B depicts interface B 420 from FIG. 4. In this embodiment, interface B 420 comprises module 1 550, 1394-1995 serial bus 525, module 1 connector 552, 1394-1995 serial bus 545, and module 2 connector 562. Interface B 420 comprises two modules connected by 1394-1995 serial bus 525 and 545 to provide greater functionality to the user of the electronic medical device diagnostic system, primarily so that module 1 may be more readily portable. Module 1 550 comprises input device 510, optional connector 516, and optional A/D converter 520. Optional connector 516 and optional A/D converter 520 are only necessary if input device 510 produces analog signals. Module 2 560 comprises network interface module 530 and physical network connector 540. By segregating the components in interface B 420, the transportability of module 1 may increase due to the less complex nature of the components in module 1 550. Module 1 550 interfaces with module 2 560 via 1394-1995 serial bus 525 to module 1 connector 552 and via 1394-1995 serial bus 545 to module 2 connector 562. For example, if input device 510 in module 1 550 represented an electronic stethoscope, the electronic stethoscope would be more useful if it were not also connected to network interface module 530 and physical network connector 540. Thus, module 1 550 only contains input device 510, optional connector 516, and optional A/D converter 520. This modularity depicted for interface B 420 would have similar benefits for other electronic medical devices.

FIG. 5C illustrates a block diagram of an interface for preparing medical information for transmission over an electronic medical device diagnostic system according to an alternative embodiment of the present invention. FIG. 5C depicts interface C 430 from FIG. 4. In this embodiment, interface C 430 comprises module 1 570, P1394.1 serial bus 517, module 1 connector 572, module 2 580, P1394.1 serial bus 546, and module 2 connector 582. Similar to interface B 420 in FIG. 5B, interface C 430 comprises two modules connected by P1394.1 serial bus 515 and 545 to provide greater functionality, except that interface C 430 is even more portable than interface B 420. Module 1 570 comprises input device 510. Module 2 580 thus comprises network interface module 530 and physical network connector 540. Note that module 2 580 does not include an A/D converter, because this alternative embodiment assumes that the electronic medical device at input device 510 produces digital signals. Therefore in interface C 430, by further segregating the components as compared to interface B 420, the transportability of module 1 570 should further increase due to the even less complex nature of the components in that module. Other than this difference, and the difference in bus configurations, interface B 420 and interface C 430 operate the same.

C. Process

The systems shown and described in connection with FIGS. 2 and 4 execute several distinct methods in collecting medical information from an electronic medical device via a serial bus for processing from a remote patient site 205 to a remote diagnostic site 130 or a remote processing center 170. These methods include facilitating the input of medical information from an electronic medical device via a serial bus at remote patient site 205, transmitting the medical information from remote patient site 205 to remote diagnostic site 130 or medical processing center 170 over network 160 or network 180, and receiving the medical information at remote diagnostic site 130, remote diagnostic site 190, or medical processing center 170 for analysis and diagnosis. The stages associated with these methods are described in connection with FIGS. 6 through 8 and can be performed in any order, unless otherwise specified or dictated by the stages themselves.

FIG. 6 depicts a flow diagram illustrating the stages performed at a remote patient site by system 400 as shown in FIG. 4. As the first stage in this process medical information is obtained from an input device connected to an electronic medical device via a serial bus at the remote patient site (stage 600). As described above, the medical information comprises at least an analog signal, which is obtained from the electronic medical device. Next, the analog signal from the input device is converted into a digital signal (stage 610). As shown in FIG. 6, if the source signal from the electronic medical device is already digital, then this conversion would not be necessary, and this stage is therefore optional. Then, using the digital signal, a data packet is constructed for transmission of the medical information over the network (stage 620). Finally, the data packet is transmitted to the network for routing to the appropriate diagnostic location (stage 630). As described above, the data packet may be routed to either a remote diagnostic site (stage 640) or a medical processing center (stage 650).

FIG. 7 depicts a flow diagram illustrating the series of stages performed at a remote diagnostic site by system 400 as shown in FIG. 4. After the medical information has been transmitted to the remote diagnostic site, the remote diagnostic site receives the data packet (stage 700). Next, the remote diagnostic site deconstructs the data packet to obtain the digital signal, which originated from an electronic medical device (stage 710). If necessary, the remote diagnostic site may also optionally convert the digital signal to an analog signal using a digital/analog (D/A) converter (stage 720). Finally, the remote diagnostic site displays or presents the medical information to a physician or medical technician for analysis and diagnosis (stage 730). Although not depicted in FIG. 7, the physician or medical technician may then respond to the patient with a diagnosis. Of course, other operations are also possible at the remote diagnostic site.

FIG. 8 depicts a flow diagram illustrating the series of stages performed at a medical processing center by system 400 as shown in FIG. 4. After the medical information has been transmitted to the medical processing center the medical processing center receives the data packet (stage 800). Next, the medical processing center deconstructs the data packet to obtain the digital signal (stage 810). At this point, the medical processing center must determine if the digital signal is for a local or remote diagnosis (stage 815). If the digital signal is intended for a local diagnosis, if necessary the medical processing center may optionally convert the digital signal to an analog signal using a D/A converter (stage 820). Then, the medical processing center displays or presents the medical information to a physician or medical technician for analysis and diagnosis (stage 830). However, if the digital signal is intended for remote diagnosis, the medical processing center reconstructs the data packet for subsequent transmission over a network (stage 840). Then, the medical processing center transmits the reconstructed data packet over the I/O module of the local network to the communications network for routing to a remote diagnostic site (stage 850). If this occurs, the data packet is processed according to the stages described in FIG. 7. Of course, other operations are also possible.

As indicated above, the processes described in FIGS. 6–8 are only illustrative, and other operations may also occur according to the present invention. In particular, the remote diagnostic site in FIG. 7 and the medical processing center in FIG. 8 may perform a number of additional operations. For example, these sites may store medical information and also have the ability to search a medical database based upon the medical information received from a patient. Also, the sites may also provide for the billing of a patient for utilization of the electronic medical device diagnostic system. Of course, these are only but a few of many other operations that can take place according to the present invention.

V. CONCLUSION

Systems consistent with the present invention overcome the disadvantages of the traditional mechanisms for obtaining a medical diagnosis from a remote location. By providing for the input of medical information from an electronic medical device via a serial bus at a remote patient site, the systems of the invention as disclosed herein provide for the processing of medical information over a network to a remote location, which overcome the shortcomings of the present systems and methods. The analysis and diagnosis of the medical information from an electronic medical device may occur at either a remote diagnostic site or a medical processing center. Further, a medical processing center can not only analyze and diagnose medical information but also route medical information to another remote diagnostic site. Still other alternative embodiments are also possible for an electronic medical device diagnostic system, which processes medical information from an electronic medical device via a serial bus for transmission and receipt over a network to obtain the diagnosis from a physician or medical technician.

As described above, therefore, it will be apparent to those skilled in the art that various modifications and variations can be made in the methods and apparatus of the present invention without departing from the spirit and scope of the invention. Thus, it is intended that the present invention cover the modifications and variations of this invention, provided they come within the scope of the appended claims and their equivalents. In this context, equivalents mean each and every implementation for carrying out the functions recited in the claims, even if not explicitly described herein.

What is claimed is:

1. A method of processing by a computer medical information obtained from a modular electronic medical device, comprising the stages of:
   receiving medical information from the modular electronic medical device via a serial bus at a remote patient site, where the modular electronic medical device at the remote patient site further comprises a first module for receiving medical input data with a first connector having a first module serial bus and a second module for interfacing with a network connection with a second connector having a second module serial bus, wherein the first connector connects with the second connector, and where the type of medical input data is selected from the group consisting of a camera, a camcorder, a stethoscope, an EKG, and an EEG;
   processing the medical information for transmission over a network;
   transmitting the medical information over the network;
   receiving the medical information at a remote diagnostic site over the network;
   processing the medical information for analysis and diagnosis at the remote diagnostic site; and
   making the medical information available at the remote diagnostic site for analysis and diagnosis.

2. The method of claim 1, wherein the serial bus is a universal serial bus, a high performance serial bus according to the IEEE 1394-1995 standard, or a high performance serial bus according to the IEEE P1394.1 standard.

3. A method of processing by a computer medical information obtained from a modular electronic medical device, comprising the stages of:
   inputting an analog signal from the modular electronic medical device connected to a patient via a serial bus at a remote patient site, where the modular electronic medical device at the remote patient site further comprises a first module for receiving medical input data with a first connector having a first module serial bus and a second module for interfacing with a network connection with a second connector having a second module serial bus, wherein the first connector connects with the second connector, and where the type of medical input data is selected from the group consisting of a camera, a camcorder, a stethoscope, an EKG, and an EEG;
   converting the analog signal into a digital signal at the remote patient site;
   processing the digital signal via a serial bus;
   constructing a data packet containing the digital signal at the remote patient site for transmission over a network;
   transmitting the data packet at the remote patient site over the network;
   receiving the data packet at the remote diagnostic site over the network;
   deconstructing the data packet at the remote diagnostic site to obtain the digital signal;
   converting the digital signal into an analog signal at the remote diagnostic site; and
   making the analog signal available at the remote diagnostic site for analysis and diagnosis by a physician or a medical technician.

4. The method of claim 1, wherein the network is the Internet, an intranet, or an extranet.

5. The method of claim 1, wherein the making stage further includes using an output device, wherein the output device is a terminal, e-mail, voice mail, printer, or fax.

6. The method of claim 1, wherein the making stage further includes allowing a physician or medical technician to review the medical information and make a diagnosis.

7. A system for processing by a computer medical information obtained from a modular electronic medical device, comprising:
   a remote patent site receiving component configured to receive medical information from the modular electronic medical device via a serial bus at a remote patient site, where the modular electronic medical device at the remote patient site further comprises a first module for receiving medical input data with a first connector having a first module serial bus and a second module for interfacing with a network connection with a second connector having a second module serial bus, wherein the first connector connects with the second connector, and where the type of medical input data is selected from the group consisting of a camera, a camcorder, a stethoscope, an EKG, and an EEG;
   a remote patient site processing component configured to process the medical information for transmission over a network;
   a transmitting component configured to transmit the medical information over the network;

a remote diagnostic site receiving component configured to receive the medical information at a remote diagnostic site over the network;

a remote diagnostic site processing component configured to process the medical information for analysis and diagnosis at the remote diagnostic site; and a making component configured to make the medical information available at the remote diagnostic site for analysis and diagnosis.

8. The system of claim 7, wherein the serial bus is a universal serial bus a high performance serial bus according to the IEEE 1394-1995 standard, or a high performance serial bus according to the IEEE P1394.1 standard.

9. The method of claim 3, wherein the serial bus is a universal serial bus, a high performance serial bus according to the IEEE 1394-1995 standard, or a high performance serial bus according to the IEEE P1394.1 standard.

10. The system of claim 7, wherein the network is the Internet, an intranet, or an extranet.

11. The system of claim 7, wherein the making component further includes a using component configured to use an output device, wherein the output device is a terminal, e-mail, voice mail, printer, or fax.

12. The system of claim 7, wherein the making component further includes an allowing component configured to allow a physician or medical technician to review the medical information and make a diagnosis.

13. A computer readable medium having computer readable code therein for processing by a computer medical information obtained from a modular electronic medical device, the computer readable code comprising:

a remote patient site receiving module configured to receive medical information from the modular electronic medical device via a serial bus at a remote patient site, where the modular electronic medical device at the remote patient site further comprises a first module for receiving medical input data with a first connector having a first module serial bus and a second module for interfacing with a network connection with a second connector having a second module serial bus, wherein the first connector connects with the second connector, and where the type of medical input data is selected from the group consisting of a camera, a camcorder, a stethoscope, an EKG, and an EEG;

a processing module configured to process the medical information for transmission over a network;

a transmitting module configured to transmit the medical information over the network;

a remote diagnostic site receiving module configured to receive the medical information at a remote diagnostic site over the network;

a remote diagnostic site processing module configured to process the medical information for analysis and diagnosis at the remote diagnostic site; and a making module configured to make the medical information available at the remote diagnostic site for analysis and diagnosis.

14. A system for processing by a computer medical information obtained from a modular electronic medical device when received over a network, comprising the stages of:

a receiving component configured to receive a data packet containing medical information over a network at a remote location;

a processing component configured to process the data packet; and an obtaining component configured to obtain from the medical information a signal, which originated from a moduler electronic medical device connected to a patient via a serial bus at a remote patient site, where the modular electronic medical device at the remote patient site further comprises a first module for receiving medical input data with a first connector having a first module serial bus and a second module for interfacing with a network connection with a second connector having a second module serial bus, wherein the first connector connects with the second connector, and where the type of medical input data is selected from the group consisting of a camera, a camcorder, a stethoscope, an EKG, and an EEG.

15. The system of claim 14, wherein the processing stage further comprises:

a first converting component configured to convert the data packet into a digital signal; and a second converting component configured to convert the digital signal into an analog signal at an analog/digital converter.

16. A system for processing by a computer medical information obtained from a modular electronic medical device, comprising:

an inputting component configured to input an analog signal from the modular electronic medical device connected to a patient via a serial bus at a remote patient site, where the modular electronic medical device at the remote patient site further comprises a first module for receiving medical input data with a first connector having a first module serial bus and a second module for interfacing with a network connection with a second connector having a second module serial bus, wherein the first connector connects with the second connector, and where the type of medical input data is selected from the group consisting of a camera, a camcorder, a stethoscope, an EKG, and an EEG;

a remote patient site converting component configured to convert the analog signal into a digital signal at the remote patient site;

a processing component configured to process the digital signal via a serial bus;

a constructing component configured to construct a data packet containing the digital signal at the remote patient site for transmission over a network;

a transmitting component configured to transmit the data packet at the remote patient site over the network;

a receiving component configured to receive the data packet at the remote diagnostic site over the network;

a deconstructing component configured to deconstruct the data packet at the remote diagnostic site to obtain the digital signal;

a remote diagnostic site converting component configured to convert the digital signal into an analog signal at the remote diagnostic site; and a making component configured to make the analog signal available at the remote diagnostic site for analysis and diagnosis by a physician or a medical technician.

17. The system of claim 16, wherein the serial bus is a universal serial bus, a high performance serial bus according to the IEEE 1394-1995 standard, or a high performance serial bus according to the IEEE P1394.1 standard.

18. A method of processing by a computer medical information obtained from a modular electronic medical device, comprising the stages of:

inputting a digital signal representing medical information from the modular electronic medical device connected to a patient via a serial bus at a remote patient site, where the modular electronic medical device at the remote patient site further comprises a first module for receiving medical input data with a first connector having a first module serial bus and a second module for interfacing with a network connection with a second connector having a second module serial bus, wherein the first connector connects with the second connector, and where the type of medical input data is selected from the group consisting of a camera, a camcorder, a stethoscope, an EKG, and an EEG;

constructing a data packet containing the digital signal at the remote patient site for transmission over a network;

transmitting the data packet at the remote patient site over the network;

receiving the data packet at a medical processing center over the network;

deconstructing the data packet at the medical processing center to obtain the digital signal; and transmitting the digital signal from the medical processing center to a diagnosis location for analysis and diagnosis by a physician or a medical technician.

19. The method of claim 18, wherein the serial bus is a universal serial bus, a high performance serial bus according to the IEEE 1394-1995 standard, or a high performance serial bus according to the IEEE P1394.1 standard.

20. The method of claim 18, further comprising storing the medical information at the remote patient site.

21. The method of claim 18, further comprising storing the medical information at the medical processing center.

22. The method of claim 18, further comprising providing for interactive communication between the remote patient site and the medical processing center for instant retrieval and diagnosis of medical information.

23. The method of claim 18, further comprising transmitting a diagnosis to the patient at the remote patient site.

24. The method of claim 18, wherein the outputting stage further includes viewing an image representing the medical information about the patient.

25. The method of claim 18, further comprising searching a medical database at the medical processing center.

26. The method of claim 18, further comprising billing the patient at the medical processing center.

27. The method of claim 18, wherein the diagnosis location is at the medical processing center.

28. The method of claim 18, wherein the diagnosis location is at a remote diagnostic site.

29. The method of claim 28, wherein the transmitting stage further includes constructing a data packet at the medical processing center for transmission over a network and transmitting the data packet via an in/out module at the medical processing center over the network to the remote diagnostic site.

30. The method of claim 18, wherein the remote patient site is a home of the patient.

31. The method of claim 28, wherein the remote diagnostic site is a hospital.

32. A system for processing by a computer medical information obtained from a modular electronic medical device, comprising:

an inputting component configured to input a digital signal representing medical information from the modular electronic medical device connected to a patient via a serial bus at a remote patient site, where the modular electronic medical device at the remote patient site further comprises a first module for receiving medical input data with a first connector having a first module serial bus and a second module for interfacing with a network connection with a second connector having a second module serial bus, wherein the first connector connects with the second connector, and where the type of medical input data is selected from the group consisting of a camera, a camcorder, a stethoscope, an EKG, and an EEG;

a constructing component configured to construct a data packet at the remote patient site for transmission over a network;

a remote patient site transmitting component configured to transmit the data packet at the remote patient site over the network;

a receiving component configured to receive the data packet at a medical processing center over the network;

a deconstructing component configured to deconstruct the data packet at the medical processing center to obtain the digital signal; and a medical processing center transmitting component configured to transmit the digital signal from the medical processing center to a diagnosis location for analysis and diagnosis by a physician or a medical technician.

33. A method of preparing by a computer medical information obtained from a modular electronic medical device for transmission over a network, comprising the stages of:

inputting an analog signal representing medical information from the modular electronic medical device connected to a patient via a serial bus at a remote patient site, where the modular electronic medical device at the remote patient site further comprises a first module for receiving medical input data with a first connector having a first module serial bus and a second module for interfacing with a network connection with a second connector having a second module serial bus, wherein the first connector connects with the second connector, and where the type of medical input data is selected from the group consisting of a camera, a camcorder, a stethoscope, an EKG, and an EEG;

processing the medical information for transmission over a network; and transmitting the medical information at the remote patient site over the network.

34. The method of claim 33, wherein the inputting stage further comprises:

receiving the analog signal at an input device via a serial bus; and converting the analog signal into a digital signal at an analog/digital converter.

35. The method of claim 34, wherein the processing stage further comprises:

constructing a data packet containing the digital signal for transmission over a network at a network interface module; and providing for transmission of the data packet via a physical network connector.

36. The method of claim 33, wherein the inputting stage further comprises receiving the analog signal at an input device via a serial bus.

37. The method of claim 36, wherein the processing stage further comprises:
- converting the analog signal into a digital signal at an analog/digital converter;
- constructing a data packet containing the digital signal for transmission over a network at a network interface module; and
- providing for transmission of the data packet via a physical network connector.

38. A system for preparing by a computer medical information obtained from a modular electronic medical device for transmission over a network, comprising:
- an inputting component configured to input an analog signal representing medical information from the modular electronic medical device connected to a patient via a serial bus at a remote patient site, where the modular electronic medical device at the remote patient site further comprises a first module for receiving medical input data with a first connector having a first module serial bus and a second module for interfacing with a network connection with a second connector having a second module serial bus, wherein the first connector connects with the second connector, and where the type of medical input data is selected from the group consisting of a camera, a camcorder, a stethoscope, an EKG, and an EEG;
- a processing component configured to process the medical information for transmission over a network; and
- a transmitting component configured to transmit the medical information at the remote patient site over the network.

39. The system of claim 38, wherein the inputting stage further comprises:
- a receiving component configured to receive the analog signal at an input device via a serial bus; and
- a converting component configured to convert the analog signal into a digital signal at an analog/digital converter.

40. The system of claim 39, wherein the processing stage further comprises:
- a constructing component configured to construct a data packet containing the digital signal for transmission over a network at a network interface module; and
- a providing component configured to provide for transmission of the data packet via a physical network connector.

41. The system of claim 38, wherein the inputting component further comprises a receiving component configured to receive the analog signal at an input device via a serial bus.

42. The system of claim 41, wherein the processing component further comprises:
- a converting component configured to convert the analog signal into a digital signal at an analog/digital converter;
- a constructing component configured to construct a data packet containing the digital signal for transmission over a network at a network interface module; and
- a providing component configured to provide for transmission of the data packet via a physical network connector.

43. A method of processing by a computer medical information obtained from a modular electronic medical device when received over a network, comprising the stages of:
- receiving a data packet containing medical information over a network at a remote location;
- processing the data packet; and
- obtaining from the medical information a signal, which originated from a modular electronic medical device connected to a patient via a serial bus at a remote patient site, where the modular electronic medical device at the remote patient site further comprises a first module for receiving medical input data with a first connector having a first module serial bus and a second module for interfacing with a network connection with a second connector having a second module serial bus, wherein the first connector connects with the second connector, and where the type of medical input data is selected from the group consisting of a camera, a camcorder, a stethoscope, an EKG, and an EEG.

44. The method of claim 43, wherein the processing stage further comprises:
- converting the data packet into a digital signal; and
- converting the digital signal into an analog signal at an analog/digital converter.

45. The method of claim 43, further comprising making the signal available at the remote location for analysis and diagnosis by a physician or medical technician.

46. The method of claim 43, wherein the remote location is a remote diagnostic site or a medical processing center.

47. The system of claim 14, further comprising a making component configured to make the signal available at the remote location for analysis and diagnosis by a physician or medical technician.

48. The system of claim 14, wherein the remote location is a remote diagnostic site or a medical processing center.

* * * * *

UNITED STATES PATENT AND TRADEMARK OFFICE
CERTIFICATE OF CORRECTION

PATENT NO. : 6,598,084 B1
DATED : July 22, 2003
INVENTOR(S) : Eric D. Edwards et al.

It is certified that error appears in the above-identified patent and that said Letters Patent is hereby corrected as shown below:

<u>Title page,</u>
Item [57], ABSTRACT,
Line 15, "center the" should read -- center, the --.

<u>Column 4,</u>
Line 14, "10" should read -- 110 --.

<u>Column 7,</u>
Line 33, "FIG. SC" should read -- FIG. 5C --.
Line 39, "serial bus 515 and 545" should read -- serial bus 517 and 546 --.

<u>Column 10,</u>
Line 50, "a remote patent" should read -- a remote patient --.

Signed and Sealed this

Sixth Day of January, 2004

JAMES E. ROGAN
*Director of the United States Patent and Trademark Office*